(12) United States Patent
Kishimoto et al.

(10) Patent No.: US 12,127,618 B2
(45) Date of Patent: Oct. 29, 2024

(54) SIZE DETERMINATION APPARATUS AND SIZE DETERMINATION METHOD FOR CLOTHING WITH CUPS

(71) Applicant: WACOAL CORP., Kyoto (JP)

(72) Inventors: Taizou Kishimoto, Kyoto (JP); Aiko Fuyuki, Kyoto (JP); Eiji Yamada, Kyoto (JP)

(73) Assignee: WACOAL CORP., Kyoto (JP)

( * ) Notice: Subject to any disclaimer, the term of this patent is extended or adjusted under 35 U.S.C. 154(b) by 523 days.

(21) Appl. No.: 17/434,562

(22) PCT Filed: Mar. 2, 2020

(86) PCT No.: PCT/JP2020/008770
§ 371 (c)(1),
(2) Date: Aug. 27, 2021

(87) PCT Pub. No.: WO2020/179754
PCT Pub. Date: Sep. 10, 2020

(65) Prior Publication Data
US 2022/0125144 A1 Apr. 28, 2022

(30) Foreign Application Priority Data
Mar. 5, 2019 (JP) .................. 2019-039954

(51) Int. Cl.
*A41H 1/02* (2006.01)
*A41C 5/00* (2006.01)

(52) U.S. Cl.
CPC .............. *A41H 1/02* (2013.01); *A41C 5/00* (2013.01)

(58) Field of Classification Search
CPC .......... A41H 1/02; A41C 5/00; A61B 5/1073; G06Q 30/0282; G06Q 30/0631; G06Q 30/0641; G06Q 30/0621
See application file for complete search history.

(56) References Cited

U.S. PATENT DOCUMENTS

| | | | | |
|---|---|---|---|---|
| 5,485,855 A | * | 1/1996 | Shiraiwa | A41H 1/02 600/587 |
| 8,397,391 B2 | * | 3/2013 | Ohly | A41C 3/00 33/2 R |

(Continued)

FOREIGN PATENT DOCUMENTS

| CN | 206137238 U | 5/2017 |
|---|---|---|
| CN | 107156976 A | 9/2017 |

(Continued)

OTHER PUBLICATIONS

"Cups", Wikipedia, URL: zh.wikipedia.org/zh-tw/%E7%BD%A9%E6%9D%AF, Oct. 3, 2022.

(Continued)

*Primary Examiner* — Yaritza Guadalupe-McCall
(74) *Attorney, Agent, or Firm* — Leydig, Voit & Mayer, Ltd.

(57) ABSTRACT

A brassiere size determination apparatus for clothing with cups covering a user's bust includes an acquisition unit and a determination unit. The acquisition unit acquires a first volume of at least a lower part of the bust. The determination unit determines a cup size of clothing with cups based on the first volume of the lower part.

5 Claims, 9 Drawing Sheets

(56) References Cited

U.S. PATENT DOCUMENTS

| | | | |
|---|---|---|---|
| 8,549,763 B2* | 10/2013 | Krawchuk | A41B 9/00 2/243.1 |
| 8,832,955 B2* | 9/2014 | Petter | A41H 1/02 33/759 |
| 9,440,399 B2 | 9/2016 | Pettis et al. | |
| 9,568,296 B2* | 2/2017 | Moore | A61B 5/4312 |
| 10,018,466 B2* | 7/2018 | Laan | G06Q 30/0631 |
| 10,238,155 B2* | 3/2019 | Braverman | A41C 3/0092 |
| 10,390,571 B2* | 8/2019 | McKeen | A41C 3/128 |
| 10,973,271 B2* | 4/2021 | D'Antonio | G01B 3/1061 |
| 10,976,157 B2* | 4/2021 | Redenius | G01B 11/285 |
| 11,430,246 B2* | 8/2022 | Pei | G06Q 30/0621 |
| 2009/0287119 A1* | 11/2009 | Chapman | A41H 1/02 600/587 |
| 2014/0019087 A1* | 1/2014 | Bengtson | A61B 5/4312 702/155 |
| 2015/0342266 A1* | 12/2015 | Cooper | A41H 1/10 705/26.7 |
| 2016/0076884 A1 | 3/2016 | Laan et al. | |
| 2020/0000165 A1* | 1/2020 | Wang | A41H 1/00 |
| 2022/0125144 A1* | 4/2022 | Kishimoto | G06Q 30/0631 |
| 2022/0335641 A1* | 10/2022 | Fantegrossi | G06V 40/103 |
| 2022/0391958 A1* | 12/2022 | Yeom | G06Q 30/0282 |
| 2023/0040804 A1* | 2/2023 | Rushton | A41C 3/0021 |
| 2023/0354939 A1* | 11/2023 | Douglas | A41H 1/02 |
| 2023/0376644 A1* | 11/2023 | Chou | G06F 30/17 |

FOREIGN PATENT DOCUMENTS

| | | | | |
|---|---|---|---|---|
| JP | 2001117963 A | * | 4/2001 | |
| JP | 2009-030194 A | | 2/2009 | |
| TW | 201439800 A | | 10/2014 | |
| TW | 201728289 A | | 8/2017 | |
| WO | WO-2018146109 A1 | * | 8/2018 | A61B 5/1072 |

OTHER PUBLICATIONS

Japanese Patent Office, International Search Report in International Application No. PCT/JP2020/008770, mailed May 26, 2020.

Lee et al., "Measurement protocol of women's nude breasts using a 3D scanning technique", *Applied Ergonomics*, vol. 35, No. 4, pp. 353-359, (2014).

International Bureau, International Preliminary Report on Patentability (IPRP) in counterpart International Application No. PCT/JP2020/008770, mailed Sep. 16, 2021.

\* cited by examiner

| UNDERBUST SIZE | | 65 | 70 | 75 | 80 | 85 | 90 |
|---|---|---|---|---|---|---|---|
| DETERMINATION EQUATION | | k1=a,k2=b | k1=a,k2=b | $V_c = k_1 \times A + k_2 \times T$ k1=a,k2=c | k1=a,k2=c | k1=a,k2=d | k1=a,k2=d |
| SIZE DETERMINATION | A-B | B65/A65 | B70/A70 | B75/A75 | B80/A80 | B85/A85 | B90/A90 |
| | B-C | C65/B65 | C70/B70 | C75/B75 | C80/B80 | C85/B85 | C90/B90 |
| | C-D | D65/C65 | D70/C70 | D75/C75 | D80/C80 | D85/C85 | D90/C90 |
| | D-E | E65/D65 | E70/D70 | E75/D75 | E80/D80 | E85/D85 | E90/D90 |
| | E-F | F65/E65 | F70/E70 | F75/E75 | F80/E80 | F85/E85 | F90/E90 |
| | F-G | G65/F65 | G70/F70 | G75/F75 | G80/F80 | G85/F85 | G90/F90 |
| | G OR MORE | G65 OR MORE | G70 OR MORE | G75 OR MORE | G80 OR MORE | G85 OR MORE | G90 OR MORE |

SIZE DETERMINATION APPARATUS AND SIZE DETERMINATION METHOD FOR CLOTHING WITH CUPS

CROSS-REFERENCE TO RELATED APPLICATIONS

This patent application is the U.S. National Stage of International Patent Application No. PCT/JP2020/008770, filed Mar. 2, 2020, which claims the benefit of Japanese Patent Application No. 2019-039954, filed Mar. 5, 2019, which are each incorporated by reference.

TECHNICAL FIELD

The present disclosure relates to a size determination apparatus and a size determination method for clothing with cups.

BACKGROUND ART

Custom-made systems for clothing or underclothes are formerly known. For example, Patent Document 1 describes a custom-made system for underclothes. In this system, a measured value of a predetermined portion of the user's body is measured by a three-dimensional body measurement apparatus, and based on the measured value, template data corresponding to the user's ideal body type is generated. After the preference information is compared with the counseling information, the final sewing information is determined and the underclothes such as a brassiere is manufactured. Patent Document 2 describes a data three dimensions apparatus for generating three-dimensional shape data. In this apparatus, three-dimensional shape data obtained by optically reading an actual human body is used. Then, three-dimensional shape data indicating the human body shape of a client is generated using the side view and the front view obtained by photographing the client.

CITATION LIST

Patent Literature

Patent Document

[Patent Document 1] JP 2009-30194 A
[Patent Document 2] JP 2001-117963 A

SUMMARY OF INVENTION

Technical Problem

As described above, techniques for customizing a underclothes such as a brassiere are known. Meanwhile, in a underclothes department or the like, it is required to propose or recommend a brassiere (clothing with cups) fitted to the body of a user from among a group of brassieres having various sizes. Top and underbust girths are often used to determine the size of a brassiere that fits a user's body. For example, a store clerk at the underclothes department measures these parts, determines the underbust size from the underbust girth, and determines the cup size from the difference between the top bust girth and the underbust girth. In some cases, the store clerk selects a plurality of sizes and types of brassieres that are likely to fit the user, and lets the user to try on the brassiere and choose a product.

Meanwhile, a three-dimensional scanner (3D scanner) capable of acquiring body shape information may be used for proposal or recommendation to a user. A three-dimensional scanner can also determine the underbust size and cup size of the brassiere. For example, it is conceivable to determine the cup size that fits the user based on the three-dimensional bust shape. However, when many users are targeted, the size and shape of the bust are different for each user, and the shape of each bust is complicated. There are limitations to determine the size of clothing with cups to fit each user's body by traditional apparatus and methods.

The present disclosure describes a size determination apparatus and method that can determine the size of clothing with cups to fit each user's body.

Solution to Problem

One aspect of the present disclosure is a size determination apparatus for clothing with cups covering a user's bust including an acquisition unit which acquires a volume of at least a lower part of the bust and a determination unit which determines a cup size of clothing with cups based on the volume of the lower part.

According to this clothing with cups size determination apparatus, the cup size of clothing with cups is determined based on the volume of the lower part of the user's bust. The volume of the lower part can have a larger influence on the cup size than the volume of the entire bust. Therefore, if at least the volume of the lower part is used for determination, it is possible to select the cup size that better fits the user's body. Therefore, even when many users are targeted, the size of clothing with cups that fits the body of each user can be determined.

The acquisition unit may acquire the volume of the entire bust including the lower part of the bust, and the determination unit may determine the cup size based on the volume of the lower part and the volume of the entire bust. For example, when the volume of the upper part of the bust is relatively small, a gap tends to be formed between the brassiere and the bust. When the volume of the upper part of the bust is relatively large, the brassiere tends to bite into the bust. In this way, by using the volume of the entire bust including the volume of the upper part in addition to the volume of the lower part as a second element, the fitting accuracy is further improved.

The size determination apparatus may include a volume conversion unit which calculates a converted volume of the bust by adding a product obtained by multiplying a volume of the lower part by a first coefficient and a product obtained by multiplying a volume of the entire bust by a second coefficient different from the first coefficient. The determination unit may determine the cup size based on the converted volume. The converted volume calculated by separately setting the first coefficient by which the volume of the lower part is multiplied and the second coefficient by which the volume of the entire bust is multiplied is easily adapted to the classification of the cup size. Determining the cup size based on the converted volume further enhances the accuracy of the fitting.

The second coefficient may be set larger as an underbust size becomes larger. The relationship between the volume of the lower part and the fittable cup size varies depending on the underbust size. By setting the second coefficient in this way, it is possible to select an appropriate cup size for each underbust size.

The determination unit may output a plurality of candidate sizes determined based on the volume of the lower part as a determination result. It is often difficult to select the only cup size that fits the user. When multiple candidate sizes are output as a determination result, room for choice is given to the user, and matching to the body or preference of the user is realized.

The volume of the lower part may be obtained by dividing the entire bust up and down at a height position in the height direction of the bust top of the bust. When the volume of the lower part is obtained based on the bust top (as a boundary), a more appropriate cup size corresponding to the bust of each user can be determined. In addition, the standard is easily standardized for all users, and the stability and reliability of determination in the determination unit are also enhanced.

Another aspect of the present disclosure is a size determination method of clothing with cups covering a user's bust, acquiring a volume of at least a lower part of the bust and determining a cup size of clothing with cups based on the volume of the lower part.

According to the size determination method of clothing with cups, the cup size of clothing with cups is determined based on the volume of the lower part of the user's bust. The volume of the lower part can have a larger influence on the cup size than the volume of the entire bust. Therefore, if at least the volume of the lower part is used for determination, it is possible to select the cup size that better fits the user's body. Therefore, even when many users are targeted, the size of clothing with cups that fits the body of each user can be determined.

Effects of Invention

According to the present disclosure, it is possible to determine the size of clothing with cups that fits the body of each user even when many users are targeted.

BRIEF DESCRIPTION OF DRAWINGS

FIG. 3 (*a*) is a diagram conceptually showing the extraction of the bust, and FIG. 3 (*b*) is a diagram conceptually showing the calculation of the volume of the lower part of the bust.

DESCRIPTION OF EMBODIMENTS

Hereinafter, embodiments of the present disclosure will be described with reference to the drawings. In the description of the drawings, same reference numerals are given to the same element, and the overlapping description will be omitted.

Figure 1:
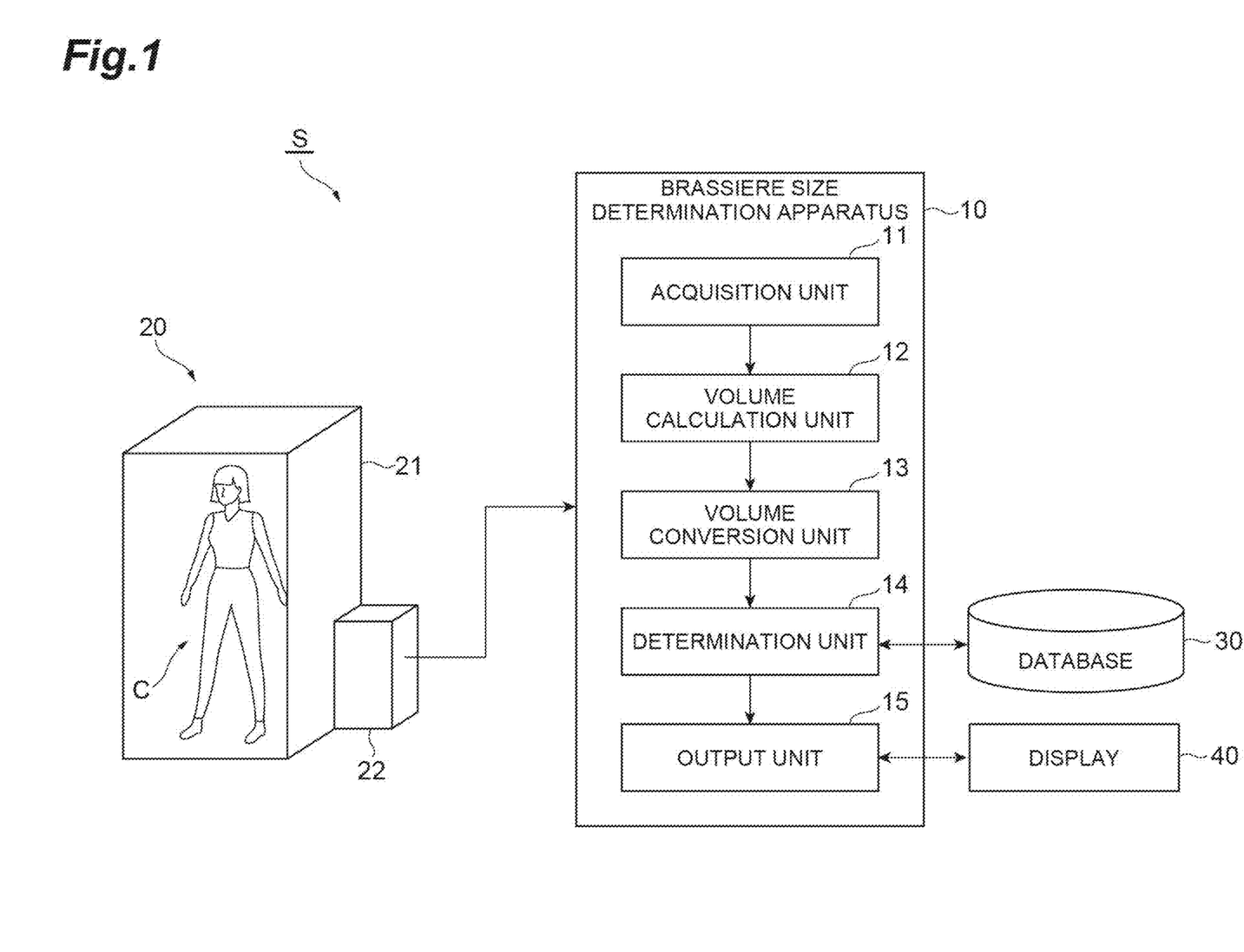
FIG. 1 is a diagram illustrating an example of a functional configuration of a size determination apparatus according to an embodiment.

Referring to FIG. 1, a brassiere size determination apparatus 10 according to the embodiment will be described. In the present embodiment, the brassiere size determination apparatus 10 is incorporated into the clothing size determination system S and constitutes a part of the clothing size determination system S. The clothing size determination system S is a system that presents or recommends underclothes fitting to the body of user C to the user C who is a customer coming to, for example, a underclothes store. The clothing size determination system S is configured to propose or recommend a fittable underclothes to a large number of users C. According to the clothing size determination system S, a plurality of three-dimensional positions on the body of the user C are measured by the 3D scanner 20, and one or more underclothes are automatically proposed or recommended based on the measured values. In the clothing size determination system S, for example, the customer service by the store clerk is unnecessary (can be omitted), and the users C can choose a underclothing (product) by themselves. That is, self-service underclothing purchases or underclothing choices are possible.

The clothing size determination system S includes a 3D scanner 20 for acquiring body shape information of the user C, and the brassiere size determination apparatus 10 for determining the size of a brassiere (clothing) with cups fitted to the user C based on a measured value output from the 3D scanner 20. The clothing size determination system S further includes a database 30 in which information on brassieres having various sizes (including sizes, types, prices, and the like) and size determination information including boundary values and the like used for size determination described later are stored, and a display 40 for displaying the information on the brassiere output from the brassiere size determination apparatus 10. Clothing with cups is an upper body garment having a pair of cups covering the left and right bust B of user C. Specific examples of clothing with cups include, in addition to brassieres, camisole with cups, one piece with cups, and the like.

Figure 3:
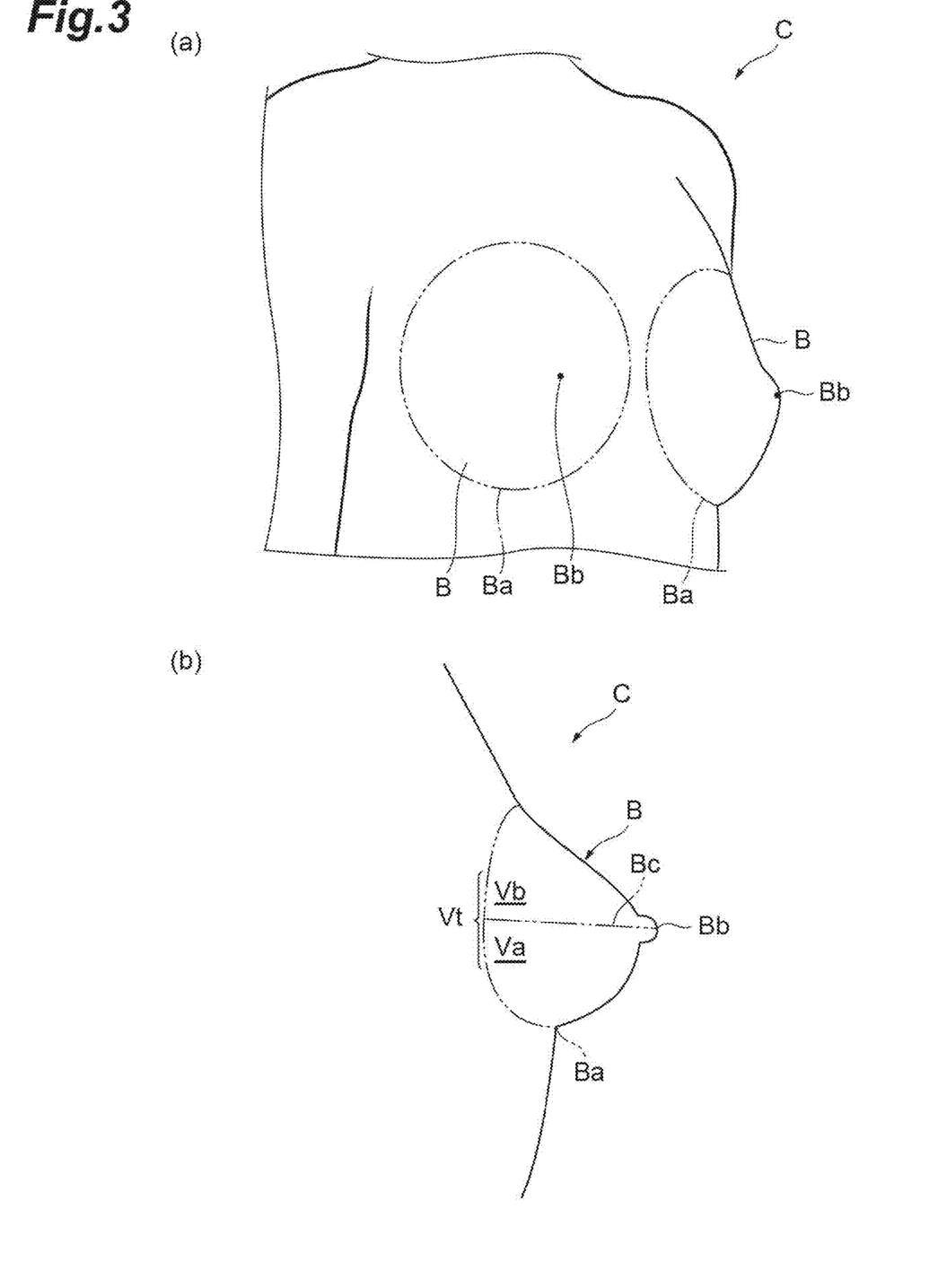

The 3D scanner 20 is, for example, an optical three-dimensional body shape measurement device. The type of the 3D scanner 20 is not particularly limited. A known infrared scanner or a known laser scanner may be used as the 3D scanner 20. In the present embodiment, the 3D scanner 20 can measure at least the shape of the upper body of the user C, that is, the shape of the body (trunk) of the user C and the shape of the bust B of the user C (see FIG. 3 (*a*)). The 3D scanner 20 includes a measurement device 21 for scanning a user C standing at the center of a rectangular apparatus, and a calculation unit 22 for inputting a measurement result by the measurement device 21, performing a predetermined calculation, and outputting body shape information. The measurement device 21 includes various sensors. The measurement device 21 transmits three-dimensional data (measurement results), which is whole-body point cloud data including the bust B of the user C, to the calculation unit 22. The calculation unit 22 includes a computer. The calculation unit 22 performs a predetermined process on the input three-dimensional data, performs a process of recognizing a measurement target portion (including the bust B and the underbust), and generates, for example, a three-dimensional image (or two-dimensional images such as front and side images).

The brassiere size determination apparatus 10 is able to transmit and receive information to and from the 3D scanner 20, the database 30, and the display 40 via a communication network. The configuration and type of each of the communication networks are not limited at all, and may be designed according to any policy. For example, the communication network may be constructed by the Internet, an intranet, or a combination thereof. The communication network may be a wired communication network, a wireless communication network, or a combination thereof.

The database 30 is an apparatus (storage unit) for storing clothing information on clothing with cups. The clothing information indicates attributes of individual clothing. The clothing information may indicate attributes of individual clothing items that can be traded for charge or free of charge. An attribute of a garment refers to a data item that characterizes the garment, for example, a shape feature, a dimension feature, a fabric feature, a member feature, a structural feature, a sewing feature, a garment pressure, or a function of the garment. The attributes of the garment may include an image (product image) of the garment.

Figure 4:
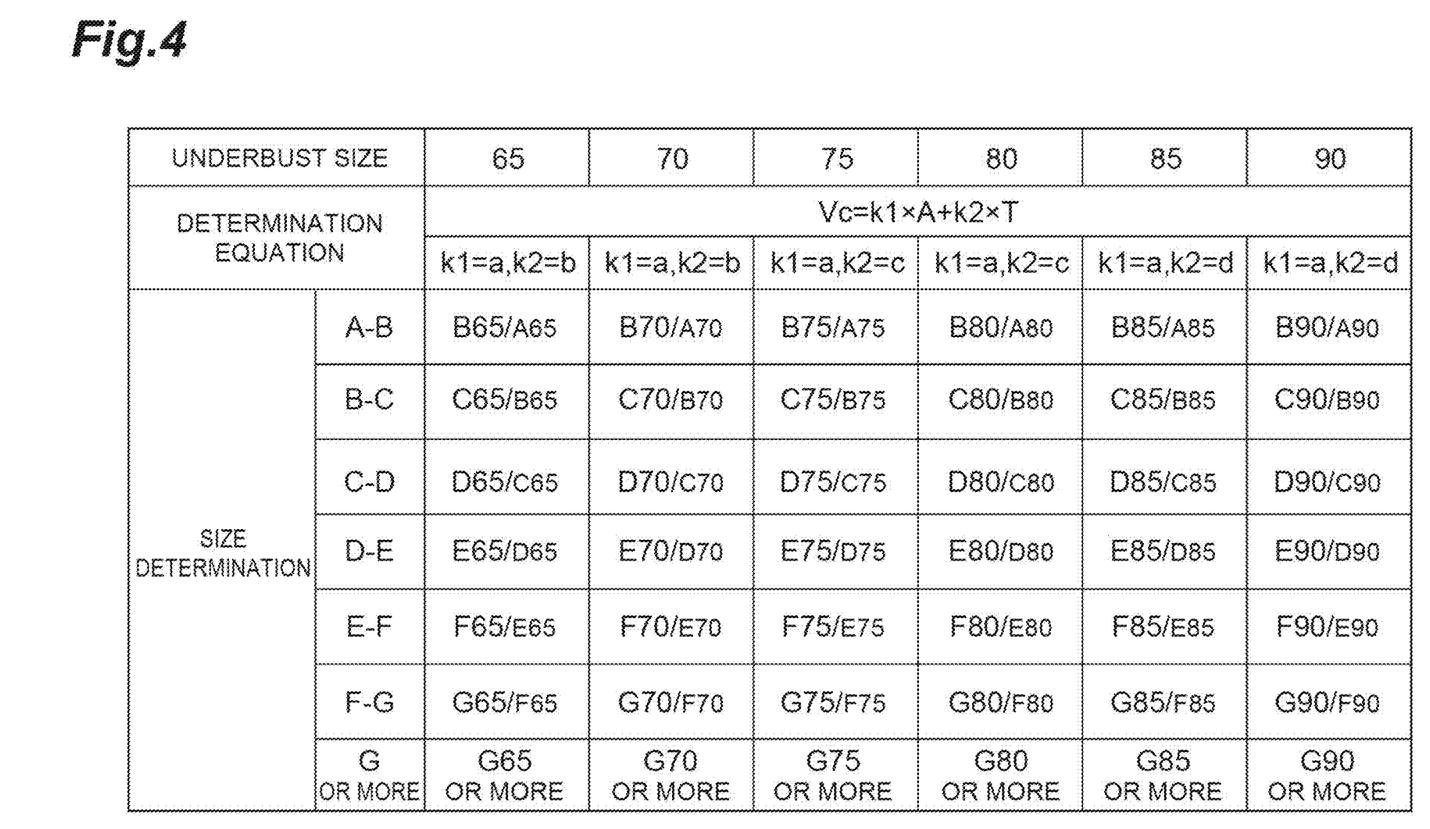
FIG. 4 is a table showing cup candidate sizes corresponding to various underbust sizes.

In the present embodiment, the clothing information includes information on the brassiere described above. Attributes of the garment include brassiere size as a dimensional feature of the garment. The brassiere size includes at least a cup size of a cup covering the user C's bust B and an underbust size corresponding to the user C's underbust girth. Underbust girth refers to the girth of the fuselage at the lowest point of bust B. As shown in FIG. 4, the cup size includes a plurality of types of sizes such as an A cup, a B cup, a C cup, a D cup, an E cup, an F cup, and a G cup. The underbust size includes a plurality of types of sizes such as 65, 70, 75, 80, 85, and 90. It should be noted that these figures are Japanese brassiere sizes on a centimeter (cm) basis, but the size determination apparatus and size determination method according to the present disclosure may be similarly applied to brassiere sizes in other countries employing standards different from Japan using the configurations and methods disclosed in the specification.

The brassiere size determination apparatus 10 includes, as a functional element, an acquisition unit 11, a volume calculation unit 12, a volume conversion unit 13, a determination unit 14, and an output unit 15. The acquisition unit 11 acquires three-dimensional information of the whole body of user C transmitted from the 3D scanner 20. In particular, the acquisition unit 11 acquires three-dimensional data of the upper body shape including the bust B of the user C.

Figure 2:
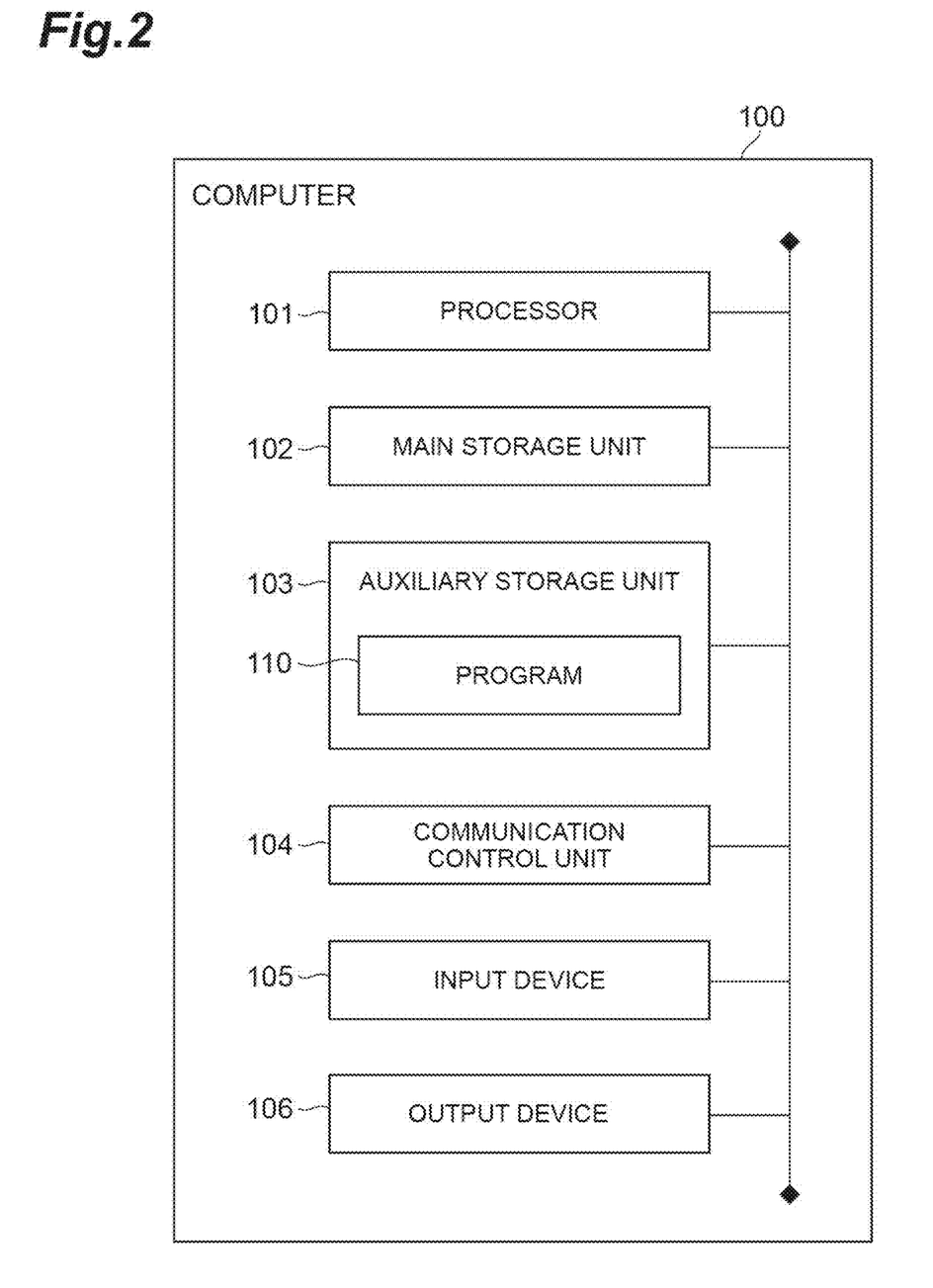
FIG. 2 is a diagram illustrating an example of a hardware configuration of a computer that can function as a size determination apparatus according to the embodiment.

FIG. 2 is a diagram illustrating an example of a hardware configuration of a computer 100 that can function as the brassiere size determination apparatus 10. For example, the computer 100 includes a processor 101, a main storage unit 102, an auxiliary storage unit 103, a communication control unit 104, an input device 105, and an output device 106. The processor 101 executes an operating system and an application program. The main storage unit 102 includes, for example, a ROM and a RAM. The auxiliary storage unit 103 is constituted by, for example, a hard disk or a flash memory, and generally stores a larger amount of data than the main storage unit 102. The auxiliary storage unit 103 stores a program 110 for causing at least one computer to function as the brassiere size determination apparatus 10. The communication control unit 104 includes, for example, a network card or a wireless communication module. The input device 105 includes, for example, a keyboard, a mouse, and a touch panel. The output device 106 includes, for example, a monitor and a speaker.

Each function element of the brassiere size determination apparatus 10 is realized by causing the processor 101 or the main storage unit 102 to read the program 110 and execute the program. The program 110 includes codes for realizing each function element of the brassiere size determination apparatus 10. The processor 101 operates the communication control unit 104, the input device 105, or the output device 106 according to the program 110, and reads and writes data in the main storage unit 102 or the auxiliary storage unit 103. Each function element of the brassiere size determination apparatus 10 is realized by this processing. Data or databases necessary for processing may be stored in the main storage unit 102 or the auxiliary storage unit 103.

The program 110 corresponds to a brassiere size determination program. The program 110 may be provided after being fixedly recorded on a tangible recording medium such as a CD-ROM, a DVD-ROM, or a semiconductor memory. Alternatively, the program 110 may be provided via a communication network as a data signal superimposed on a carrier wave.

The brassiere size determination apparatus 10 may be constituted by one or more computers. When a plurality of computers are used, these computers are connected to each other via a communication network to configure the brassiere size determination apparatus 10.

As shown in FIGS. 1, 3(a) and 3(b), the volume calculation unit 12 calculates the volume of the bust B based on the three-dimensional data of the upper body shape acquired by the acquisition unit 11. The volume calculation unit 12 extracts the range of the left and right bust B from the three-dimensional data of the upper body shape. At the lower end of the bust B, a boundary line between the bust B and the body, which is usually called Verge's line (a registered trademark in Japan), appears. This boundary line may be referred to as a lower groove line. In the three-dimensional data, since there is a portion around which the curvature changes, the volume calculation unit 12 extracts the Verge's line from the change point of the curvature. The volume calculation unit 12 extracts the boundary line from the change point of the curvature for the upper side and both the left and right sides of the bust B in the same manner as the Verge's line. By connecting these extracted Verge's lines and boundary lines to each other, an annular boundary line Ba of the bust B is generated. The volume calculation unit 12 calculates, for example, the volume of the range surrounded by the boundary line Ba as a bust volume Vt which is the volume of the entire bust.

The volume calculation unit 12 further calculates a first volume Va which is the volume of the lower part of the bust B. The bust volume Vt of the bust B corresponds to the sum of the first volume Va and the second volume Vb which is the volume of the upper part of the bust B. The volume calculation unit 12 calculates the first volume Va by splitting the bust B into two in the vertical direction at the height position of the bust B in the height direction of the bust top Bb. After obtaining the three-dimensional data of the lower part based on the three-dimensional data of the bust B, the volume calculation unit 12 may calculate the volume of the lower part from the three-dimensional data in the range below the horizontal split plane Be (horizontal plane) set at the height position of the height direction of the bust top Bb. That is, in the calculation of the first volume Va, the calculation of the bust volume Vt is not necessarily required. The first volume Va may be directly calculated from the three-dimensional data without calculating the bust volume Vt. Of course, after calculating the bust volume Vt of the bust B, the volume calculation unit 12 may calculate the second volume Vb in a range below the split plane Bc in the bust volume Vt. The volume calculation unit 12 may calculate the second volume Vb, which is the volume of the upper part of the bust B, and subtract the second volume Vb from the bust volume Vt.

The brassiere size determination apparatus 10 calculates the first volume Va in this manner by noting that the first volume Va, which is the volume of the lower part of the bust B, is an important factor in determining (choice of) the brassiere size. The second volume Vb, which is the volume of the upper part of the bust B, also relates to the determination of the brassiere size as a second factor. In the present embodiment, the bust volume Vt corresponding to the sum of the first volume Va and the second volume Vb is used as the second factor. The acquisition unit 11 and the volume calculation unit 12 correspond to an acquisition unit that acquires at least the first volume Va of the bust B. The acquisition unit 11 and the volume calculation unit 12 correspond to an acquisition unit that acquires the bust volume Vt. The brassiere size determination apparatus 10 is not limited to calculating the first volume Va and the bust volume Vt. The first volume Va and the bust volume Vt may be transmitted from the calculation unit 22 of the 3D scanner 20, and the acquisition unit 11 may acquire them.

In the present embodiment, as described above, the volume of the upper part of the bust B corresponds to the difference obtained by subtracting the first volume Va, which is the volume of the lower part of the bust B, from the bust volume Vt, which is the volume of the entire bust. That is, the volume of the entire bust is the sum of the volume of the lower part (lower half) of the bust B and the volume of the upper part (upper half) of the bust B. However, the volume of the upper part of the bust B may be defined in a different way. For example, the volume of the entire bust B may be divided into three parts. That is, the bust B may include a lower part, a middle part, and an upper part. In this case, the brassiere size may be determined based on the volume of the lower part and the volume of the upper part of the bust B. The middle part may include a bust top Bb. The brassiere size may be determined based on the volume of the lower part of the bust B and a volume of at least a portion other than the lower part of the bust B. The brassiere size may be determined based on the volume of the lower part and the volume of the middle part of the bust B.

The volume calculation unit 12 calculates the underbust girth of user C from the three-dimensional data of the upper body shape. The underbust girth may be transmitted from the calculation unit 22 of the 3D scanner 20 and acquired by the acquisition unit 11. The underbust girth may be input to the calculation unit 22 or the brassiere size determination apparatus 10 of the 3D scanner 20 by the user C.

The volume conversion unit 13 calculates the converted volume of the bust B based on a predetermined determination equation. As described above, the first volume Va and the bust volume Vt are used to determine the brassiere size. The volume conversion unit 13 uses these 2 values to calculate the converted volume Vc of the bust B. The brassiere size determination apparatus 10 stores a first coefficient k1, which is a weighting coefficient multiplied by the first volume Va, and a second coefficient k2, which is a weighting coefficient multiplied by the bust volume Vt, according to a plurality of underbust sizes. The first coefficient k1 and the second coefficient k 2 are, for example, positive values.

The determination equation in the present embodiment is represented by the following formula (1) (See also FIG. 4)

$$Vc = k1 \times A + k2 \times T \quad (1)$$

Wherein:
Vc: the converted volume
A: the first volume Va
k1: the first coefficient
T: the bust volume Vt
k2: the second coefficient That is, the volume conversion unit 13 calculates the converted volume Vc of the bust B by adding the product obtained by multiplying the first volume Va of the lower part by the first coefficient k1 and the product obtained by multiplying the bust volume Vt by the second coefficient k2. The second coefficient k2 may be a value different from the first coefficient k1. The second coefficient k2 may be smaller than the first coefficient k1. The second coefficient k2 may be greater than the first coefficient k1. As shown in FIG. 4, the first coefficient k1 ((a) in the figure) may be constant regardless of the underbust size. The second coefficient k2 may be set larger as the underbust size becomes larger. In the first coefficient k1 and the second coefficient k2 shown in FIG. 4, the magnitude relationship between the coefficients may be b<a<c<d. The second coefficient k2 is, for example, the same in underbust sizes 65 and 70 ((b) in the figure), the same in underbust sizes 75 and 80 ((c) in the figure), and the same in underbust sizes 85 and 90 ((d) in the figure). The second coefficient k2 may be set so as to change more greatly according to the underbust size than the first coefficient k1. That is, depending on the underbust size, the first coefficient k1 may be relatively unchanged or constant, while the second coefficient k2 may be relatively largely changed. Even in this case, the second coefficient k2 is set larger as the underbust size becomes larger. Such a setting of the first and second coefficients allows suitable weighting in the converted volume.

Figure 7:
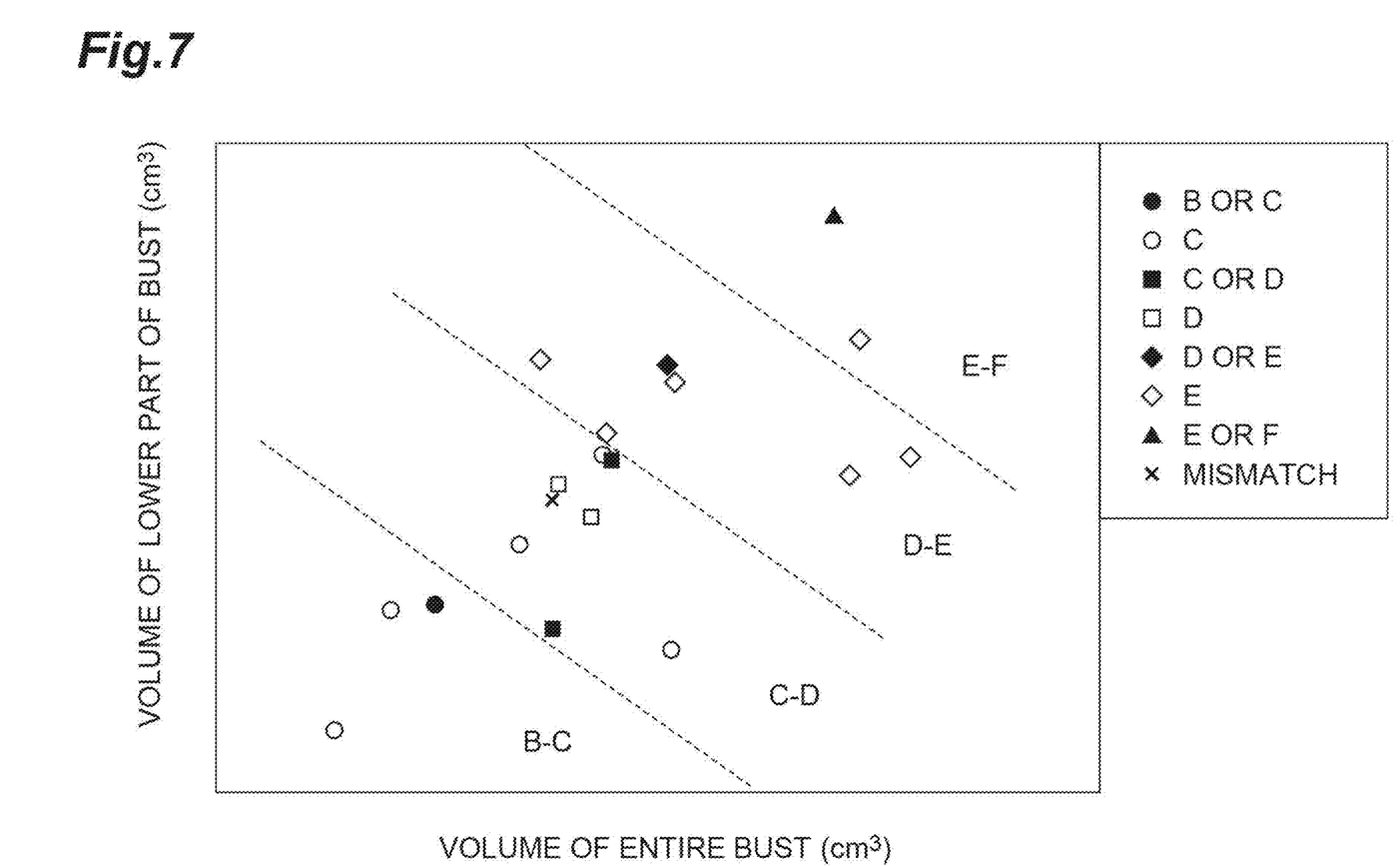
FIG. 7 is a graph showing the distribution of the volumes of the lower part with respect to the volumes of the entire bust and the cup candidate sizes.

The first coefficient k1 and the second coefficient k2 may be determined for each underbust size based on the test shown in FIGS. 7 and 8 described later. When the first coefficient k1, the second coefficient k2, and the boundary value of the converted volume Vc (described later) are determined so that the degree of coincidence of the cup size is high, the accuracy and reliability of the brassiere size determination apparatus 10 are improved.

The determination unit 14 determines the underbust size of the brassiere (underbust candidate size) fitted to the user C based on the underbust girth calculated by the volume calculation unit 12. The determination unit 14 determines the cup size of the brassiere (cup candidate size) fitted to the user C based on at least the first volume Va of the lower part of the bust B. That is, the determination unit 14 determines the underbust candidate size and the cup candidate size based on the girth of the underbust and the first volume Va. These are the most important parts of the brassiere size that brassiere size determination apparatus 10 recommends to user C. The underbust candidate size can also be referred to as a fittable underbust size. The cup candidate size may also be referred to as a fittable cup size.

Figure 5:
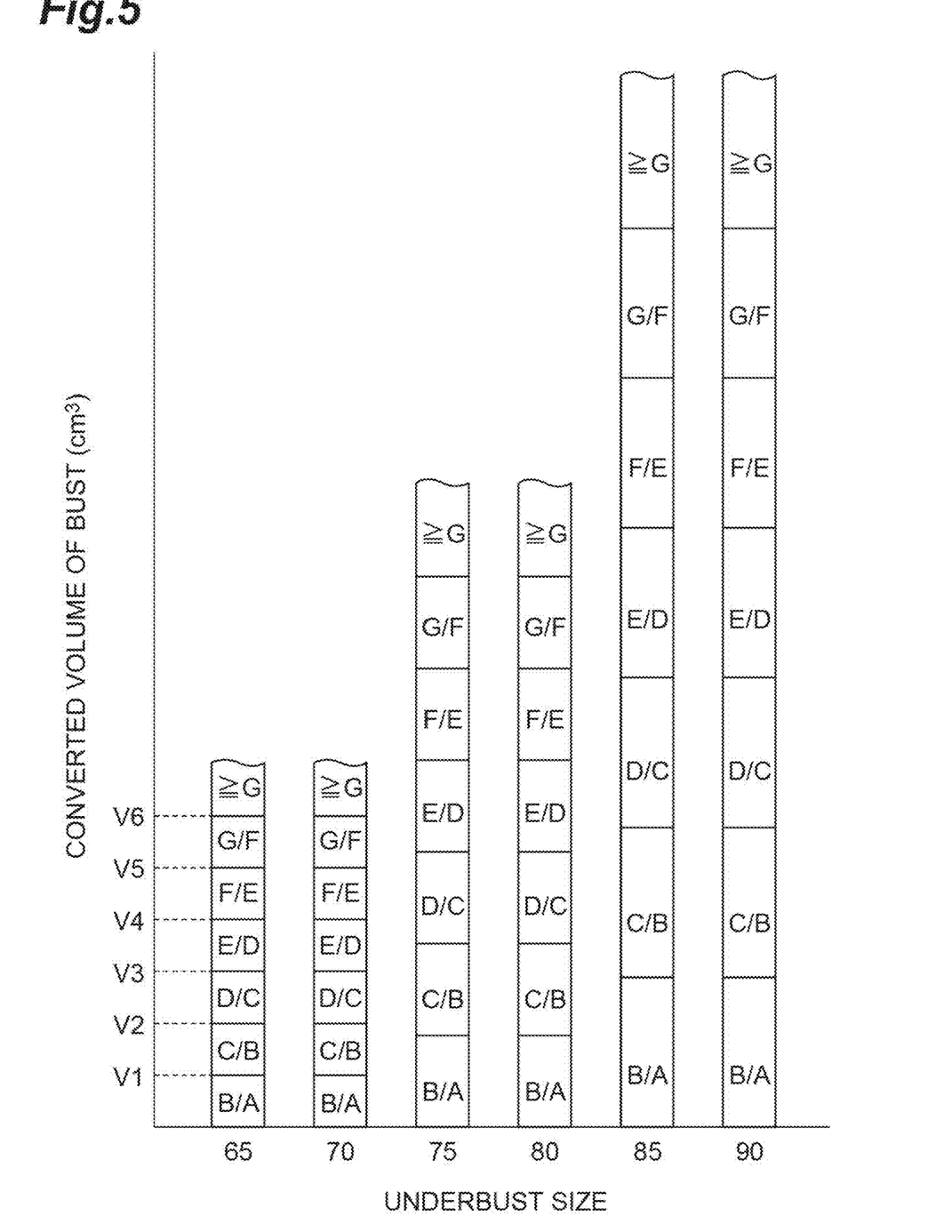
FIG. 5 is a diagram conceptually showing boundary values of converted volumes and cup candidate sizes in the cup size determination of FIG. 4.

Referring to FIGS. 4 and 5, the method for determining the brassiere size in the determination unit 14 will be described in more detail. FIG. 4 is a table showing cup candidate sizes corresponding to various underbust sizes. FIG. 5 conceptually shows the boundary value of the converted volume and the cup candidate size in the cup size determination of FIG. 4. As shown in FIG. 4, in the brassiere size determination apparatus 10, for example, six kinds of underbust sizes shown in the figure are set. Depending on the girth of the underbust, any underbust size is selected as the underbust candidate size. For example, a boundary value (such as 67.5 cm and 72.5 cm) may be set between two adjacent underbust sizes (such as 65 cm and 70 cm, 70 cm and 75 cm). Further, a plurality of cup sizes are set corresponding to each underbust size. In these cup size determinations, the converted volume Vc calculated by the above-described determination equation (1) is used.

More specifically, as shown in FIG. 5, the boundary value of the converted volume Vc (V1 to V6, and the like) is set corresponding to each underbust size. In each area between two adjacent boundary values, two types of cup sizes are set. For example, when the underbust size is 70 and the converted volume Vc is a value between the boundary values V2 and V3, the D-cup or the C-cup is selected as the cup candidate size. Then, as shown in FIG. 4, D70 or C70 is selected as the brassiere candidate size. As shown in FIG. 4, when the converted volume Vc is an area within a range from C to D, a larger D-cup may be offered as a first candidate, and a smaller C-cup may be offered as a second candidate. In FIG. 4, one with a larger font and shown first corresponds to the first candidate. In FIG. 5, the first one corresponds to the first candidate.

In this way, the determination unit 14 determines the cup size that fits the user C based on the converted volume Vc. That is, the determination unit 14 determines the cup size that fits the user C based on the first volume Va and the bust volume Vt. The determination unit 14 outputs two candidate sizes determined based on the first volume Va and the bust volume Vt as determination results. In offering the two candidate sizes, the determination unit 14 may assign priorities to the candidate sizes. The priority is the degree of recommendation. When the two candidate sizes are offered, the determination unit 14 may equally offer the two candidate sizes without giving priority to the candidate sizes. When the priority is given, the candidate size having a higher degree of recommendation may be displayed larger. The candidate size having a higher degree of recommendation may be displayed first (in displaying order or temporally). A description for recommendation such as "this size is recommended" may be added to the candidate size having a higher degree of recommendation.

In the determination of the cup size, as shown in FIG. 5, the width between two adjacent boundary values may increase as the underbust size increases. The width between boundary values is the same in underbust sizes 65 and 70 (V1 to V6 in the figure), in underbust sizes 75 and 80, and in underbust sizes 85 and 90, for example. The data structure in the brassiere size determination apparatus 10 is not limited to one shown in FIGS. 4 and 5, and may be designed arbitrarily.

The determination unit 14 determines the underbust size and the cup size of the brassiere by the determination method described above. The determination unit 14 may acquire a plurality of product informations (candidate brassieres) matching the determination result from the database 30. The determination unit 14 outputs size information indicating the determination result and product information corresponding thereto to the output unit 15. The output unit 15 outputs the information output from the determination unit 14 to the display 40. The output unit 15 outputs the information of the candidate brassiere to the display 40.

Figure 6:
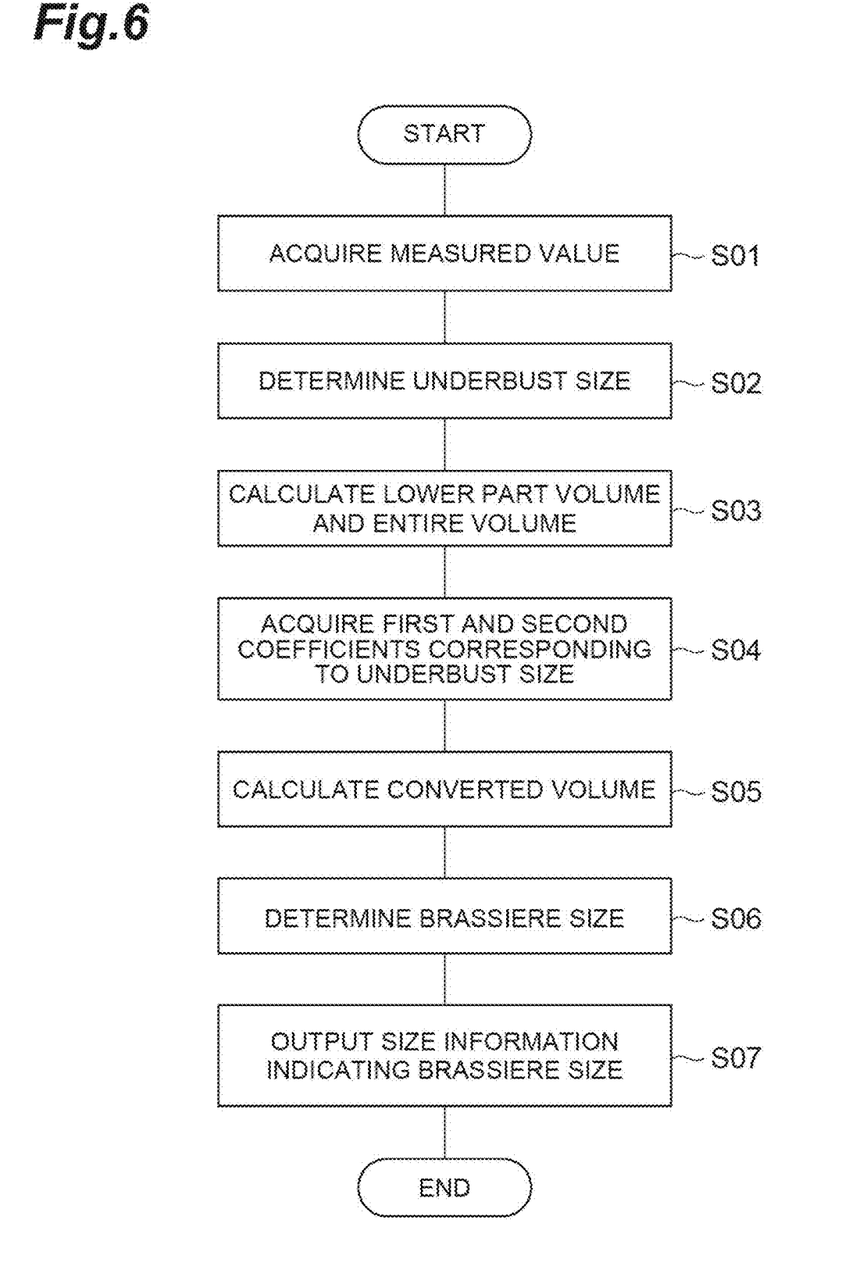
FIG. 6 is a flowchart showing the procedure of the size determination process by the size determination apparatus.

Referring to FIG. 6, the operation of the brassiere size determination apparatus 10 and the brassiere size determination method according to the present embodiment will be described. As shown in FIG. 6, first, in step S01, the acquisition unit 11 of the brassiere size determination apparatus 10 acquires three-dimensional information of the whole body of user C transmitted from the 3D scanner 20 as a measured value. The three-dimensional data includes three-dimensional data of an upper body shape. Next, the volume calculation unit 12 may calculate the underbust girth of user C from the three-dimensional data of the upper body shape.

In step S02, the determination unit 14 determines the underbust size of the brassiere fitted to the user C by comparing the girth of the underbust with the boundary value. Next, in step S03, the volume calculation unit 12 extracts the range of the left and right bust B from the three-dimensional data of the upper body shape, and calculates the first volume Va and the bust volume Vt.

Subsequently, in step S04, the volume conversion unit 13 acquires the first coefficient k1 and the second coefficient k2 corresponding to the underbust size. Here, coefficient a and either coefficient b or c or d shown in FIG. 4 are acquired according to the underbust size that fits user C. In step S05, the volume conversion unit 13 calculates the converted volume Vc of the bust B by substituting the numerical values for the two volumes calculated in step S03 into the determination equation (equation (1)).

In step S06, the determination unit 14 determines a brassiere size to be fitted to the user C shown in FIGS. 4 and 5. In step S07, the output unit 15 outputs size information indicating the determined brassiere size. Through the series of processes described above, the recommended brassiere size and product information suitable to the user C are displayed on the display 40, for example.

According to the brassiere size determination apparatus 10 of the present embodiment, the cup size of the brassiere is determined based on the first volume Va of the lower part of the bust B of the user C. The first volume Va of the lower part may have a larger influence on the cup size than the bust volume Vt. Therefore, if at least the first volume Va of the lower part is used for determination, it is possible to select the cup size that better fits the body of the user C. Therefore, even when many users C are targeted, the size of the brassiere that fits the body of each user C can be determined.

For example, when the first volume Va of the upper part of the bust B is relatively small, a gap tends to be formed between the brassiere and the bust B. If the second volume Vb of the upper part of the bust B is relatively large, the brassiere tends to bite into the bust B. In this way, by using the bust volume Vt including the volume of the upper part in addition to the first volume Va of the lower part as the second element, the fitting accuracy is further improved.

(Entire Bust Volume)

The converted volume Vc calculated by separately setting the first coefficient k1 by which the first volume Va of the lower part is multiplied and the second coefficient k2 by which the bust volume Vt of the lower part is multiplied is easily fitted to the classification of the cup size. Determining the cup size based on the converted volume Vc further enhances the accuracy of fitting.

Here, the usefulness of the determination formula of the present embodiment will be described with reference to FIGS. 7 and 8. FIG. 7 is a graph showing the distribution of the first volume Va of the lower part with respect to the bust volume Vt and the cup candidate size. In FIGS. 7 and 8 nineteen subjects were asked to self-report the cup sizes that they considered fit, and the volumes of the busts of the subjects separately measured by the 3D scanner 20 were plotted on a graph. The test data shown in FIGS. 7 and 8 are test data in a population having an underbust size of 70. The boundary line corresponding to the boundary value of the determination formula of the present embodiment is represented as a broken line extending obliquely on the graph. As shown in FIG. 7, by setting these broken lines as boundary lines, the fittable cup size according to the self-report matched the cup size of the area delimited by the boundary lines in eighteen out of nineteen persons (matching rate is 95%). (It should be noted that only one data of a subject who reported that the fittable cup size was neither C cup nor D cup is plotted in the area from C to D.)

Figure 8:
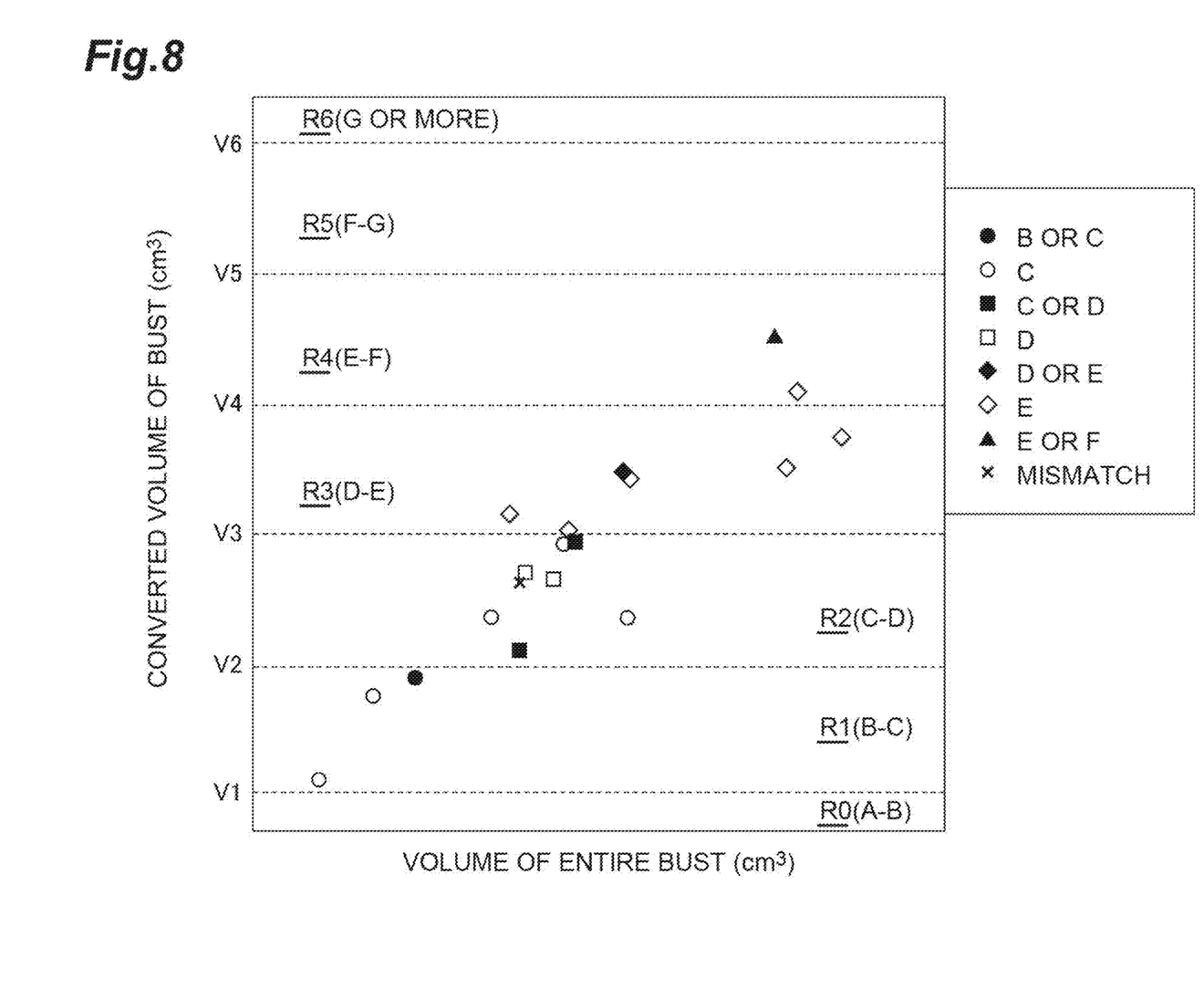
FIG. 8 is a graph showing the distribution of converted volumes versus entire bust volumes and cup candidate sizes.

FIG. 8 is a graph showing the distribution of the converted volume Vc with respect to the bust volume Vt and the cup candidate size. As shown in FIG. 8, in the underbust size 70, the first coefficient k1 and the second coefficient k2 are set so that the boundary lines are horizontal. The boundary lines showing a high matching rate in FIG. 7 are converted by the determination formula and become the boundary values of the converted volume Vc (see V1 to V6 shown in FIG. 5). It can be read that the cup sizes are adapted to the areas R1 to R6, which are areas partitioned by V1 to V6 after the conversion by the conversion formula, with a matching rate of 95%. As described above, if the determination formula and the first and second coefficients are prepared so that the boundary line becomes horizontal by drawing the boundary line so that the matching rate becomes high in the plot of FIG. 7, a high matching rate can be obtained. These determination formulas and the first and second coefficients are set for each underbust size as described above.

In this embodiment, the second coefficient k2 is set larger as the underbust size becomes larger. The relationship between the first volume Va of the lower part and the fittable cup size varies depending on the underbust size. By setting the second coefficient k2 in this manner, it is possible to select an appropriate cup size for each underbust size.

It is often difficult to select the only cup size that fits user C. When multiple candidate sizes are output as a determination result, room for choice is given to user C, and matching to the body or preference of user C is realized.

As for the portion of the brassiere above the bust top portion (a portion covering the bust top Bb), the range covering the upper part of the bust B of the user C often varies depending on the design of the product. On the other hand, as for the portion below the bust top portion, the range covering the lower part of the bust B of the user C is not changed in most products. That is, the portion of the brassiere below the bust top portion covers all or substantially all of the lower part of the bust B of user C in most products. When the first volume Va of the lower part is obtained based on the bust top Bb (as a boundary), a more appropriate cup size can be determined according to the bust B of each user C. Further, the standard is easily unified for all users C, and the stability and reliability of determination in the determination unit 14 are also enhanced.

Figure 9:
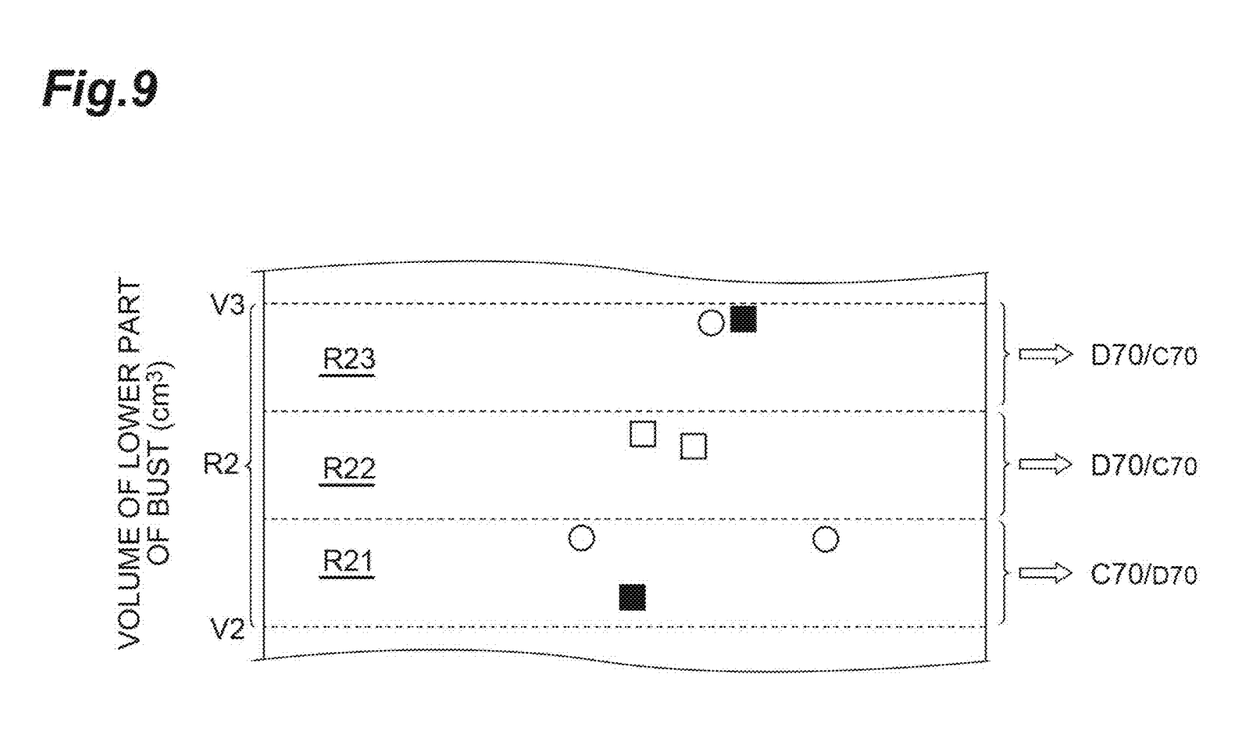
FIG. 9 is a diagram for explaining a modification of the cup candidate size selection method.

Although the embodiments of the present disclosure have been described above, the present disclosure is not limited to the above embodiments. For example, as shown in FIG. 9, the range of the converted volume Vc in a certain area (e.g., area R2) may be split into 3 equal parts, areas R21, R22, and R23 may be set in ascending order, and the larger area (D-cup in the illustrated example) may be set as the first candidate when the area R23 or R22 is satisfied, and the smaller area (C cup in the illustrated example) may be set as the first candidate when the area R21 is satisfied. This is merely an example, and n equal parts (n is an integer of 2 or more) other than three equal parts may be used, and which of the larger and smaller parts is set as the first candidate can be arbitrarily determined.

The first volume Va is not limited to the aspect in which the first volume Va is obtained based on the height position in the height direction of the bust top Bb. For example, the first volume Va may be calculated from three-dimensional data in a range below a predetermined height position in the height direction among the three-dimensional data of the bust B. A volume ratio to the bust volume Vt may be determined in advance based on the three-dimensional data of the bust B, and the first volume Va may be calculated based on the volume ratio.

The determination of brassiere size may not take into account the bust volume Vt. That is, the brassiere size may be determined based on only the first volume Va. Based on the first volume Va and the second volume Vb, a bra size may be determined.

The determination unit 14 may output only one candidate size. In this case, for example, the determination method illustrated in FIG. 9 may be applied to offer only the first candidate as the candidate size. The determination unit 14 may output 3 candidate sizes. In this case, the center candidate size of the 3 sizes may be preferentially offered.

The cup size of clothing with cups may be determined based only on the volume of the lower part of the bust B of user C. In this case, the cup size of clothing with cups may be determined based on the volume of the lower part of the bust B of the user C and a correspondence relationship similar to that shown in FIGS. 4 and 5.

The size determination method of clothing with cups is not limited to the case of being performed by a computer, and may be performed by, for example, a store clerk of an underclothes department. The store clerk may estimate the volume corresponding to the first volume Va of the lower part based on the difference between the girth of the top bust and the girth of the underbust of the bust B of the customer user C and the outer shape (appearance) of the bust B, and select the brassiere size based on the volume. In this case, the entire volume corresponding to the bust volume Vt may be added.

INDUSTRIAL APPLICABILITY

According to the present disclosure, it is possible to determine the size of clothing with cups that fits the body of each user even when many users are targeted.

REFERENCE SIGNS LIST

10 . . . brassiere size determination apparatus (size determination apparatus), 11 . . . acquisition unit, 12 . . . volume calculation unit, 13 . . . volume conversion unit, 14 . . . determination unit, 15 . . . output unit, 20 . . . 3D scanner, 30 . . . database, 100 . . . computer, 101 . . . processor, B . . . bust, Ba . . . boundary line, Bb . . . bust top, Bc . . . split plane, C . . . user, S . . . clothing size determination system, Va . . . first volume (volume of lower part), Vb . . . Second volume (volume of upper part), Vc . . . converted volume, Vt . . . bust volume (volume of entire bust).

The invention claimed is:

1. A size determination apparatus for clothing with cups covering a user's bust comprising:

an acquisition unit configured to acquire a volume of a lower part of the bust, and a volume of an entire bust including the lower part of the bust, and a determination unit configured to determine a cup size of the clothing with cups based on the volume of the lower part of the bust and the volume of the entire bust including the volume of the lower part of the bust.

2. The size determination apparatus according to claim 1, further comprising:
- a volume conversion unit which configured to calculate a converted volume of the bust by adding a product obtained by multiplying the volume of the lower part by a first coefficient and a product obtained by multiplying the volume of the entire bust by a second coefficient different from the first coefficient, and
- wherein the determination unit is configured to determine the cup size based on the converted volume.

3. The size determination apparatus according to claim 2, wherein the second coefficient is set larger as an underbust size becomes larger.

4. The size determination apparatus according to claim 1, wherein the determination unit is configured to output a plurality of candidate sizes determined based on the volume of the lower part as a determination result.

5. The size determination apparatus according to claim 1, wherein the volume of the lower part is obtained by splitting an entire bust into upper and lower parts at a height position in a height direction of a bust top of the bust.

\* \* \* \* \*